United States Patent
Schlosser et al.

(10) Patent No.: US 6,964,746 B2
(45) Date of Patent: Nov. 15, 2005

(54) MIXTURE OF A PHOSPHONITE WITH OTHER COMPONENTS

(75) Inventors: Elke Schlosser, Augsburg (DE); Wolfgang Wanzke, Augsburg (DE); Christian Lechner, Hurlach (DE)

(73) Assignee: Clariant GmbH, Frankfurt (DE)

(*) Notice: Subject to any disclaimer, the term of this patent is extended or adjusted under 35 U.S.C. 154(b) by 0 days.

(21) Appl. No.: 10/459,976

(22) Filed: Jun. 12, 2003

(65) Prior Publication Data

US 2004/0051088 A1 Mar. 18, 2004

(30) Foreign Application Priority Data

Jun. 14, 2002 (DE) .......................... 102 26 732

(51) Int. Cl.$^7$ .................. C09K 21/10; C09K 21/12; C09K 15/32; C08K 5/49; C08K 5/51
(52) U.S. Cl. ................. 252/609; 252/400.24; 252/401; 252/407; 252/389.24; 252/390; 252/396; 252/182.29; 106/18.18; 524/115; 524/126; 524/128; 524/135; 524/153; 524/151
(58) Field of Search ................ 252/602, 609, 252/400.24, 401, 407, 389.24, 390, 396, 182.29, 183.12; 106/18.18; 524/115, 126, 128, 135, 153, 151

(56) References Cited

U.S. PATENT DOCUMENTS

| | | | |
|---|---|---|---|
| 4,670,493 A | | 6/1987 | Van Asbroeck et al. .... 524/120 |
| 5,164,436 A | * | 11/1992 | Maier et al. ............... 524/290 |
| 5,324,805 A | * | 6/1994 | Kioka et al. .............. 526/348.6 |
| 5,516,827 A | * | 5/1996 | Kaufhold et al. ........... 524/397 |
| 5,616,636 A | | 4/1997 | Avar et al. .................. 524/102 |
| 5,663,284 A | * | 9/1997 | Kominami et al. ......... 528/310 |
| 6,002,004 A | * | 12/1999 | Wehner et al. .............. 544/280 |
| 6,194,494 B1 | * | 2/2001 | Wehner et al. .............. 524/100 |
| 6,255,371 B1 | | 7/2001 | Schlosser et al. ........... 524/100 |
| 6,284,857 B1 | * | 9/2001 | Shinozaki et al. .......... 526/351 |
| 6,344,158 B1 | | 2/2002 | Schlosser et al. ........... 252/609 |
| 6,362,358 B1 | | 3/2002 | Gronmaier et al. ........... 558/95 |
| 6,547,992 B1 | | 4/2003 | Schlosser et al. ........... 252/609 |
| 6,686,041 B2 | * | 2/2004 | Sakamoto et al. .......... 428/402 |
| 2001/0034420 A1 | * | 10/2001 | Honma et al. .............. 525/439 |

FOREIGN PATENT DOCUMENTS

| | | |
|---|---|---|
| DE | 199 20 276 | 11/2000 |
| EP | 0 000 354 | 1/1979 |
| EP | 0 390 277 | 10/1990 |
| EP | 0 442 465 | 8/1991 |
| GB | 2 250 291 | 6/1992 |
| WO | 00/66658 | 11/2000 |

OTHER PUBLICATIONS

English abstract for EP 0 000 354, (1979).
Gächter, R., Müller, H., "Plastics Additives Handbook", 1993, Hanser Verlag, pp 40–69.
"Plastics Additives Handbook", 5$^{th}$ Edition, 2000 Carl Hanser Verlag, pp 80–96.

* cited by examiner

Primary Examiner—Joseph D. Anthony
(74) Attorney, Agent, or Firm—Anthony A. Bisulca

(57) ABSTRACT

The invention relates to mixtures of phosphonite (component A) and/or an ester and/or salt of a long-chain fatty acid (component B), and/or a carboxylic ester, and/or carboxylic amide (component C), and also to their use in polyamides or in polyesters.

13 Claims, No Drawings

MIXTURE OF A PHOSPHONITE WITH OTHER COMPONENTS

The invention relates to mixtures of a phosphonite (component A) and/or an ester and/or salt of a long-chain fatty acid (component B), and/or a carboxylic ester, and/or carboxylic amide (component C), and also to their use.

With a few exceptions, thermoplastics are processed in the melt. The associated changes in structure and state cause some alteration in the chemical structure of almost every plastic. The consequence can be crosslinking, oxidation, and molecular weight changes, and therefore also changes in physical and technical properties. To reduce the stress to which polymers are exposed during their processing, various additives are used, as required by the particular plastic. Stabilizers are generally added, and these suppress, or at least retard, the alteration processes such as crosslinking reactions or degradation reactions. Lubricants are also admixed with most plastics, and these have the primary function of improving the flow behavior of the melt.

A wide variety of additives is generally used simultaneously, each of these having its own function. For example, antioxidants and stabilizers are used so that the plastic withstands processing without damage to its chemical structure and is then resistant over long periods to external effects, such as heat, UV light, weathering, and oxygen (air). Lubricants not only improve flow behavior but also prevent excessive adhesion of the polymer melt to hot machine components, and act as dispersing agents for pigments, fillers, and reinforcing materials.

The use of flame retardants can affect the stability of the plastic during processing in the melt. Large additions of flame retarders are often necessary in order to ensure sufficient flame retardancy of the plastic to international standards. Flame retardants can adversely affect the processing stability of plastics because they have the chemical reactivity required for flame-retardant action at high temperatures. Examples of consequences are increased polymer degradation, crosslinking reactions, evolution of gases, or discoloration. These are effects which may not occur at all, or only in attenuated fashion, during the processing of plastics with no flame retardants.

Polyamides to which no flame retardants are added are generally stabilized by small amounts of copper halides, or else by aromatic amines and sterically hindered phenols, the emphasis being placed here on achieving long-term stability at high long-term service temperatures (H. Zweifel (Ed.): "Plastics Additives Handbook", 5$^{th}$ Edition, Carl Hanser Verlag, Munich, 2000, pp. 80–96). Polyesters, too, need antioxidant stabilization, essentially for long-term service, rather than for processing.

EP 0 442 465 A1 describes thermoplastic molding compositions which comprise halogenated flame retardants and have stabilization using amines or phosphites or a combination of an amine and a phosphite.

Carbodiimides, isocyanates, and isocyanurates have proven effective for stabilizing polymer molding compositions using phosphorus-containing flame retardants (DE 199 20 276 A1).

Particularly when phosphorus-containing flame retardants are used in polyamides and polyesters, the action of the stabilizers described hitherto has proved inadequate, specifically for suppressing the effects arising during processing, e.g. discoloration and molecular weight degradation.

It is therefore an object of the present invention to provide means for auxiliaries which have an overall improved action on the plastic, in particular for polyamides and polyesters.

This object has been achieved by way of mixtures of a phosphonite (component A) and/or an ester and/or salt of a long-chain fatty acid (component B), and/or a carboxylic ester, and/or carboxylic amide (component C).

Surprisingly, it has been found that mixtures of a phosphonite (component A) and/or an ester and/or salt of a long-chain fatty acid (component B), and/or a carboxylic ester, and/or carboxylic amide (component C) markedly increase the processing stability of flame-retardant polyamides and polyesters. The inventive combinations reduce discoloration of the plastic during processing in the melt and suppress degradation of the plastics to give units with lower molecular weight.

Phosphonites of the Structure

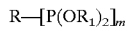

$$R-[P(OR_1)_2]_m \quad (I)$$

are suitable a component A,
where
R is a mono- or polyvalent aliphatic, aromatic, or heteroaromatic organic radicals, and
$R_1$ is a group of the structure (II)

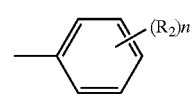

(II)

or the two radicals $R_1$ form a bridging group of the structure (III)

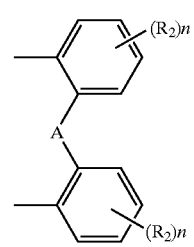

(III)

where
A is a direct bond, O, S, $C_{1-18}$-alkylene (linear or branched), $C_{1-18}$-alkylidene (linear or branched), and where
$R_2$ are, independently of one another, $C_{1-12}$-alkyl (linear or branched), $C_{1-12}$-alkoxy, $C_{5-12}$-cycloalkyl, and
n is 0 to 5, and
m is from 1 to 4.
Preference is given to the following radicals
R $C_{4-18}$-alkyl (linear or branched), $C_{4-18}$-alkylene (linear or branched), $C_{5-12}$-cycloalkyl, $C_{5-12}$-cycloalkylene, $C_{6-24}$-aryl or -heteroaryl, $C_{6-24}$-arylene or $C_{6-24}$-heteroarylene, which may also have further substitution;
$R_1$ a group of the structure (II) or (III), where
$R_2$ independently of one another, $C_{1-8}$-alkyl (linear or branched), $C_{1-8}$-alkoxy, or cyclohexyl;
A direct bond, O, $C_{1-8}$-alkylene (linear or branched), $C_{1-8}$-alkylidene (linear or branched)
and
n from 0 to 3
m from 1 to 3.
Particular preference is given to the following radicals
R cyclohexyl, phenyl, phenylene, biphenyl, or biphenylene
$R_1$ a group of the structure (II) or (III), where
$R_2$ independently of one another, $C_{1-8}$-alkyl (linear or branched), $C_{1-8}$-alkoxy, cyclohexyl;

A a direct bond, O, $C_{1-6}$-alkylidene (linear or branched) and n from 1 to 3 m from 1 to 2.

Suitable components B are esters or salts of long-chain aliphatic carboxylic acids (fatty acids), these typically having chain lengths of from $C_{14}$ to $C_{40}$.

The esters are reaction products of the carboxylic acids mentioned with familiar polyhydric alcohols, e.g. ethylene glycol, glycerol, trimethylolpropane, or pentaerythritol.

The salts used of the carboxylic acids mentioned may particularly be the alkali-metal or alkaline-earth-metal salts, or the aluminum salts or zinc salts.

A preferred component B is esters or salts of stearic acid, e.g. glycerol monostearate or calcium stearate.

A preferred component B is reaction products of montan wax acids with ethylene glycol.

Preferred reaction products are a mixture of mono(montan wax acid) ester of ethylene glycol, di(montan wax acid) ester of ethylene glycol, montan wax acids and ethylene glycol.

A preferred component B is reaction products of montan wax acids with a calcium salt.

Particularly preferred reaction products are a mixture of mono(montan wax acid) ester of 1,3-butanediol, di(montan wax acid) ester of 1,3-butanediol, montan wax acids, 1,3-butanediol, calcium montanate, and the calcium salt.

Carboxylic (ester) amides are suitable as component C.

A preferred component C is a derivative of an aromatic di- or tricarboxylic (ester) amide.

A preferred derivative is N,N'-bispiperdinyl-1,3-benzenedicarboxamide.

A particularly preferred derivative is N,N'-bis(2,2,6,6-tetramethyl-4-piperdinyl)-1,3-benzenedicarboxamide.

The mixtures of the invention preferably also comprise phosphites of the formula (IV)

$$P(OR_1)_3 \qquad (IV),$$

where $R_1$ is a group of the structure (II) or (III).

Particular preference is given to phosphites which meet the above requirements and are prepared by a Friedel-Crafts reaction of an aromatic or heteroaromatic compound, such as benzene, biphenyl, or diphenyl ether, with phosphorus trihalides, preferably phosphorus trichloride, in the presence of a Friedel-Crafts catalyst, such as aluminum chloride, zinc chloride, iron chloride, etc., and a subsequent reaction with the phenols on which the structures (II) and (III) are based. Also expressly included here are mixtures with phosphites which are produced from an excess of phosphorus trihalide with the abovementioned phenols in the reaction sequence mentioned.

From this group of compounds, preference is in turn given to the following structures (V) and (VI):

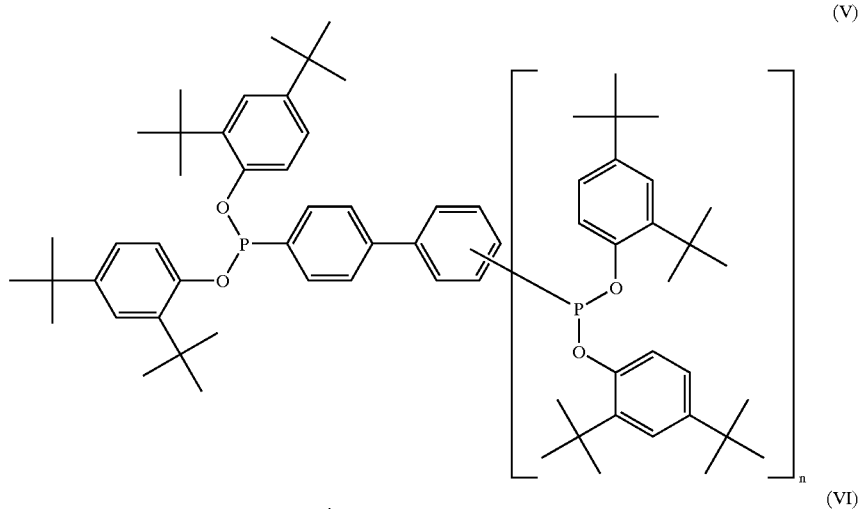

(V)

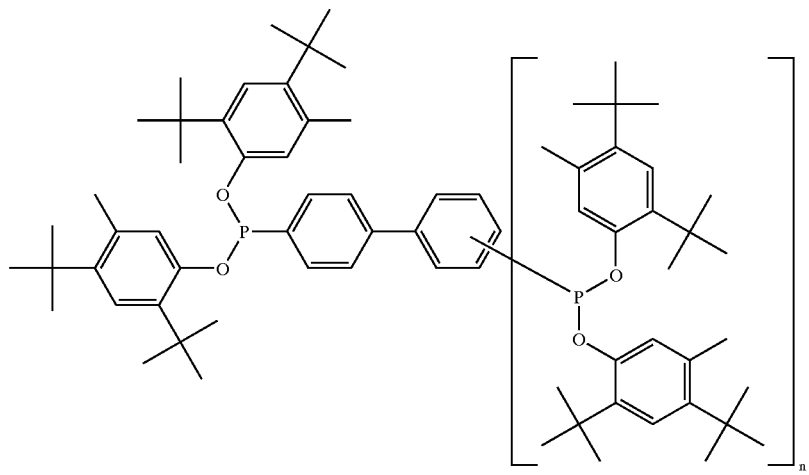

(VI)

where n may be 0 or 1, and where these mixtures may also optionally comprise the compound (VII) or, respectively, (VIII):

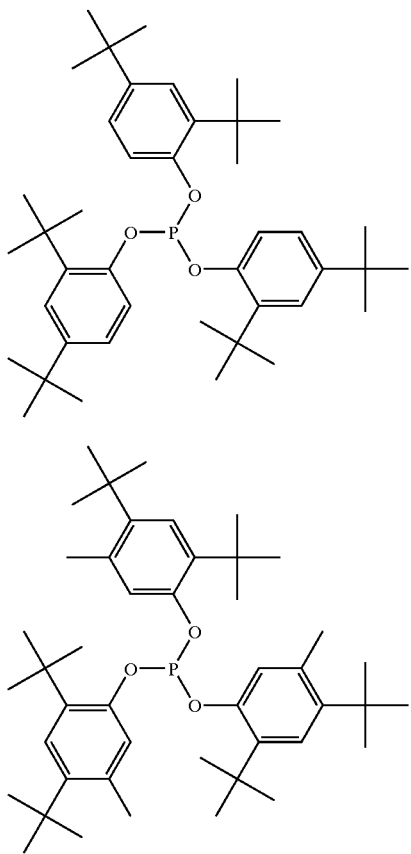

(VII)

(VIII)

The abovementioned additives may be introduced into the plastic in a very wide variety of steps in a process. For example, in the case of polyamides or polyesters, the additives may be mixed into the polymer melt at the very start of the polymerization/polycondensation, or at its end, or in a subsequent compounding process. There are also processes where the additives are added only at a later stage. This applies particularly when pigment masterbatches or additive masterbatches are used. Another possibility is that in particular pulverulent additives are applied in a drum mixer to the polymer pellets, which may be warm as a result of the drying process.

A preferred mixture comprises from 10 to 90% by weight of component A and from 90 to 10% by weight of component B or component C.

A preferred mixture comprises from 30 to 70% by weight of component A and from 70 to 30% by weight of component B or component C.

A particularly preferred mixture comprises from 45 to 55% by weight of component A and from 45 to 55% by weight of component B or component C.

A preferred mixture comprises from 10 to 90% by weight of component B and from 90 to 10% by weight of component C.

Another preferred mixture comprises from 30 to 70% by weight of component B and from 70 to 30% by weight of component C.

A particularly preferred mixture comprises from 45 to 55% by weight of component B and from 55 to 45% by weight of component C.

A preferred mixture comprises from 5 to 90% by weight of component A, from 5 to 90% by weight of component B, and from 90 to 5% by weight of component C.

A preferred mixture comprises from 15 to 70% by weight of component A, from 15 to 70% by weight of component B, and from 70 to 15% by weight of component C.

A preferred mixture comprises from 30 to 35% by weight of component A, from 30 to 35% by weight of component B, and from 35 to 30% by weight of component C.

A preferred form of components A, B, and C is pellets, flakes, fine particles, powders, and/or micronizate.

A preferred form of components A, B, and C is a physical mixture of the solids, a melt mixture, a compactate, an extrudate, or a masterbatch.

A preferred use of the mixture is in a molding composition of a polymer or of a polycondensate.

A particularly preferred use of the mixture is in a molding composition of a flame-retardant polymer or of a flame-retardant polycondensate.

For the purposes of the invention, phosphorus-containing flame retardants which may be used in polyamides or in polyesters are inorganic or organic phosphates, phosphites, hypophosphites, phosphonates, phosphinates, and phosphine oxides, and also elemental phosphorus.

Preferred phosphates are melamine phosphate, melamine pyrophosphate, and melamine polyphosphate, and also the similar melame phosphates, meleme phosphates, or melon phosphates. Ammonium polyphosphate is also preferred.

Preferred hypophosphites are calcium hypophosphite, zinc hypophosphite, and aluminum hypophosphite.

Suitable phosphinates are described in U.S. Pat. No. 6,365,071, which is expressly incorporated herein by reference.

Preferred phosphinates used are phosphinic salts of the formula (I) and/or a diphosphinic salt of the formula (II), and/or polymers of these

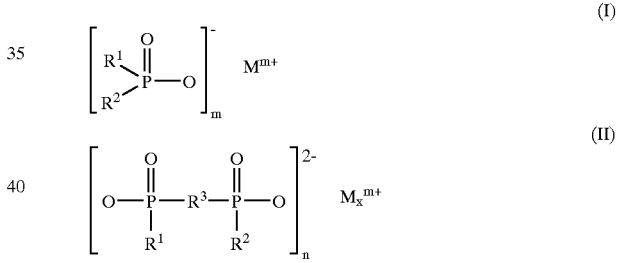

(I)

(II)

where
R$^1$ and R$^2$ are identical or different and are $C_1$–$C_6$-alkyl, linear or branched, and/or aryl;
R$^3$ is $C_2$–$C_{10}$-alkylene, linear or branched, $C_6$–$C_{10}$-arylene, $C_6$–$C_{10}$-alkylarylene, or $C_6$–$C_{10}$-arylalkylene;
M is calcium ions, aluminum ions, and/or zinc ions;
m is 2 or 3;
n is 1 or 3;
x is 1 or 2.

Preferred phosphinates are aluminum phosphinate, calcium phosphinate, and zinc phosphinate.

Elemental phosphorus which may be used is red or black phosphorus. Red phosphorus is preferred.

Any of the phosphorus-containing flame retardants used in the polycondensate may be used alone or with nitrogen-containing synergists. Typical combinations with synergists are also described in U.S. Pat. No. 6,365,071, which is expressly incorporated herein by reference.

Preferred polymers or polycondensates are polyamides. Suitable polyamides are described by way of example in DE 199 20 276 A1.

Preferred polyamides are those of amino acid type and/or of diamine/dicarboxylic acid type.

Preferred polyamides are nylon-6 and/or nylon-6,6.

Preferred polyamides are unmodified, colored, filled, unfilled, reinforced, or unreinforced polyamides, or else polyamides which have been otherwise modified.

Components A, B, and C are preferably introduced at the same or at different steps in the process during the preparation/processing of polyamides.

Other preferred polycondensates are polyesters. Suitable polyesters are described by way of example in DE 199 20 276 A1.

The polycondensates are preferably polyethylene terephthalate or polybutylene terephthalate.

Preferred polyesters are unmodified, colored, filled, unfilled, reinforced, or unreinforced polyesters, or polyesters which have been otherwise modified.

Components A, B, and C are preferably introduced at the same or at different steps in the process during the preparation/processing of polyesters.

Components A, B, and C are preferably incorporated in the polycondensation process, in the compounding process, or directly during the molding process.

A preferred total amount of components A, B, and C is from 0.01 to 10.00% by weight in the polycondensate.

A preferred total amount of components A, B, and C is from 0.1 to 2.00% by weight in the polycondensate.

A preferred total amount of flame retardant in the polymer or polycondensate is from 1 to 50% by weight.

A preferred total amount of flame retardant in the polymer or polycondensate is from 5 to 40% by weight.

A particularly preferred total amount of flame retardant in the polymer or polycondensate is from 10 to 30% by weight.

The invention preferably provides the use of organic phosphonites in combination with salts of montan wax acid and/or with aromatic di- or tricarboxylic esters and/or aromatic di- or tricarboxylic amides, as stabilizers for flame-retardant polyamides and polyesters.

The processing stability of flame-retardant polyamides and polyesters can be markedly increased using the inventive combinations of particular organic phosphonites with montan wax salts or with montan wax esters and/or with aromatic di- or tricarboxylic esters and/or with aromatic di- or tricarboxylic amides.

EXAMPLES

1. Components Used

| Commercially available polymers (pellets): | |
|---|---|
| Nylon-6,6 (GR PA 6.6): | ® Durethan AKV 30 (from Bayer AG, Germany), comprising 30% of glass fibers. |
| Polybutylene terephthalate (GR PBT): | ® Celanex 2300 GV1/30 (from Ticona, Germany), comprising 30% of glass fibers. |

Flame retardant components (pulverulent):
Aluminum salt of methylethylphosphinic acid, hereinafter termed MEPAL.
Melapur 200 (melamine polyphosphate), hereinafter termed MPP, DSM Melapur, Netherlands
Melapur® MC (melamine cyanurate), hereinafter termed MC, DSM Melapur, Netherlands
Phosphonites (component A): Sandostab® P-EPQ®, Clariant GmbH, Germany
Wax components (component B):
Licowax E, Clariant GmbH, Germany (ester of montan wax acid with ethylene glycol)
Licomont CaV 102, Clariant GmbH, Germany (Ca salt of montan wax acid)
Licowax OP, Clariant GmbH, Germany (partially Ca-saponified ester of montan wax acid)

Aromatic di- or tricarboxylic esters or aromatic di- or tricarboxylic amides (component C):
Nylostab® S-EED®, Clariant GmbH, Germany (*Nylostab S-EED is N,N'-bis(2,2,6,6-tetramethyl-4-piperidyl)-1,3-benzenedicarboxamide)

2. Preparation, Processing, and Testing of Flame-Retardant Polymer Molding Compositions The flame retardant components were mixed in the ratio given in the tables with the polymer pellets, and with the lubricants and stabilizers, and incorporated in a twin-screw extruder (Leistritz LSM 30/34) at temperatures of from 260 to 310° C. (GR PA 6.6) or from 240 to 280° C. (GR PBT). The homogenized polymer extrudate was drawn off, cooled in a water bath, and then pelletized.

After adequate drying, the molding compositions were injection molded (Arburg 320 C Allrounder) at melt temperatures of from 270 to 320° C. (GR PA 6.6) or from 260 to 280° C. (GR PBT), to give test specimens, and tested and classified for flame retardancy on the basis of the UL 94 test (Underwriters Laboratories).

The flowability of the molding compositions was determined by determining the melt volume index (MVR) at 275° C./2.16 kg. A sharp rise in the MVR value indicates polymer degradation.

Processing properties in polyester were assessed on the basis of specific viscosity (SV). The pellets of the polymer molding composition were used, after adequate drying, to prepare a 1.0% strength solution in dichloroacetic acid, and the SV values were determined. A higher SV value indicates that less polymer degradation occurred during the incorporation of the flame retardant.

Color changes were measured using a Minolta CM-3600d spectrophotometer, to DIN 6174 (L, a, b, delta E).

Unless it has been otherwise stated, for reasons of comparability, all of the experiments in each series were carried out under identical conditions (temperature programs, screw geometries, injection molding parameters, etc.).

Table 1 shows comparative examples in which a flame retardant combination based on the aluminum salt of methylethylphosphinic acid (MEPAL) and on the nitrogen-containing synergist melamine polyphosphate was used and tested, both alone and with a claimed phosphonite (component A), calcium montanate (component B), or carboxylic amide (component C) in glass-fiber-reinforced PA 6.6.

Table 2 shows the results obtained from the comparative examples presented in Table 1 after the molding compositions have been injection molded at various temperatures.

The results from the examples in which the flame retardant combinations were used together with a mixture of components A to C of the invention have been listed in Tables 3, 4, 5, and 6. All of the amounts are given as % by weight and are based on the polymer molding composition including the flame retardant combination and additives.

From the examples it is apparent that the additives of the invention (mixture of components A to C) significantly improve the processability of the polycondensates using phosphorus flame retardants and, respectively, the flame retardant combinations described, without adversely affecting flame retardancy.

Incorporation of the flame retardants into PA 6.6 leads to polymer degradation, detectable from high MVR values, and to gray-brown discoloration of the molding compositions (c1, c2). Addition of calcium montanate alone or S-EED alone cannot either improve the color of the molding compositions or substantially reduce polymer degradation (c3, c4). P-EPQ alone stabilizes the flame-retardant molding composition slightly (c5).

If a combination of components A to C is then used (e1, e2, e3, e4), marked stabilization of the flame-retardant polyamide melt can be observed, as can a substantial reduction in discoloration of the test specimens. The synergistic action of the combinations of components A to C is also clearly discernible even at relatively high processing temperatures (Table 4). The processing latitude from the polycondensates using phosphorus flame retardants can therefore be extended, and this is advantageous when the molding compositions are produced on an industrial scale.

Increased stabilization can also be achieved using Licowax E and Licowax OP in combination with polymer additives (Table 5). However, the best action is exhibited by calcium montanate.

When flame-retardant polyester (PBT) was stabilized according to the invention, a marked reduction in polymer degradation was observed, detectable in high SV figures, as was a marked reduction in discoloration (Table 6).

TABLE 1

Comparative examples (experimental series 1): flame-retardant molding compositions using components A, B, or C as single additives in glass-fiber-reinforced PA 6.6.

| Comparison | MEPAL [%] | MPP [%] | A P-EPQ [%] | B CaV 102 [%] | C S-EED [%] | UL 94 classification (0.8 mm) | MVR [cm³/10'] | Delta E*⁾ |
|---|---|---|---|---|---|---|---|---|
| c1 | 0 | 0 | 0 | 0 | 0 | n.c.**⁾ | 19 | 28 |
| c2 | 10 | 5 | 0 | 0 | 0 | V-0 | 44 | 33 |
| c3 | 10 | 5 | 1 | 0 | 0 | V-0 | 19 | 27 |
| c4 | 10 | 5 | 0 | 1 | 0 | V-0 | 58 | 32 |
| c5 | 10 | 5 | 0 | 0 | 1 | V-0 | 33 | 33 |

*⁾of test specimen, melt temperature during injection molding: 280° C.
**⁾n.c. = not classifiable

TABLE 2

Comparative examples (experimental series 1): flame-retardant molding compositions using components A, B, or C as single additives in glass-fiber-reinforced PA 6.6, using various injection molding temperatures.

| Comparison | Melt temperature during injection molding [° C.] | MVR [cm³/10'] | Delta E |
|---|---|---|---|
| c1 | 290 | 23 | 27 |
|  | 300 | 23 | 28 |
|  | 310 | 28 | 31 |
| c2 | 290 | 101 | 35 |
|  | 300 | 151 | 37 |
|  | 310 | 274 | 39 |
| c3 | 290 | 23 | 27 |
|  | 300 | 37 | 29 |
|  | 310 | 108 | 33 |
| c4 | 290 | 138 | 32 |
|  | 300 | 222 | 33 |
|  | 310 | 368 | 36 |
| c5 | 290 | 106 | 35 |
|  | 300 | 99 | 37 |
|  | 310 | 337 | 40 |

TABLE 3

Inventive examples (experimental series 1): flame-retardant molding compositions using the combination of 2 or 3 additive components in glass-fiber-reinforced PA 6.6.

| Examples | MEPAL [%] | MPP [%] | A P-EPQ [%] | B CaV 102 [%] | C S-EED [%] | UL 94 classification (0.8 mm) | MVR [cm³/10'] | Delta E*⁾ |
|---|---|---|---|---|---|---|---|---|
| e1 | 10 | 5 | 0 | 0.5 | 0.5 | V-0 | 13 | 26 |
| e2 | 10 | 5 | 0.5 | 0.5 | 0 | V-0 | 17 | 23 |
| e3 | 10 | 5 | 0.5 | 0 | 0.5 | V-0 | 12 | 30 |
| e4 | 10 | 5 | 0.33 | 0.33 | 0.33 | V-0 | 22 | 30 |

*⁾of test specimen, melt temperature during injection molding: 280° C.

TABLE 4

Inventive examples (experimental series 1): flame-retardant molding compositions using the combination of 2 or 3 additive components in glass-fiber-reinforced PA 6.6, using various injection molding temperatures.

| Examples | Melt temperature during injection molding [° C.] | MVR [cm³/10'] | Delta E |
|---|---|---|---|
| e1 | 290 | 54 | 27 |
|  | 300 | 82 | 28 |
|  | 310 | 118 | 32 |
| e2 | 290 | 35 | 25 |
|  | 300 | 64 | 26 |
|  | 310 | 130 | 27 |
| e3 | 290 | 42 | 30 |
|  | 300 | 77 | 30 |
|  | 310 | 151 | 30 |
| e4 | 290 | 44 | 30 |
|  | 300 | 44 | 31 |
|  | 310 | 69 | 30 |

TABLE 5

Inventive examples (experimental series 2): flame-retardant molding compositions using the combination of various B components, and A and C in glass-fiber-reinforced PA 6.6.

| Experiments | ME PAL [%] | MPP [%] | B wax [%] | A P-EPQ [%] | C S-EED [%] | UL 94 classification (0.8 mm) | MVR [cm³/10'] | Delta E* |
|---|---|---|---|---|---|---|---|---|
| c7 | 10 | 5 | 0 | 0 | 0 | V-0 | 41 | 38 |
| e4 | 10 | 5 | CaV 102 0.5 | 0.5 | 0.5 | V-0 | 16 | 29 |
| e5 | 10 | 5 | Wax E 0.5 | 0.5 | 0.5 | V-0 | 19 | 32 |
| e6 | 10 | 5 | Wax OP 0.5 | 0.5 | 0.5 | V-0 | 19 | 29 |

*)of test specimen, melt temperature during injection molding: 280° C.

TABLE 6

Flame-retardant molding compositions using various combinations of components A and B in glass-fiber-reinforced PBT.

| Experiments | MEPAL [%] | MC [%] | A P-EPQ [%] | B wax [%] | UL 94 classification (1.6 mm) | SV | Delta E |
|---|---|---|---|---|---|---|---|
| c8 | 10 | 10 | 0 | 0 | V-0 | 815 | 18 |
| c9 | 10 | 10 | 0.3 | 0 | V-0 | 892 | 16 |
| c10 | 10 | 10 | 0 | Wax OP 0.4 | V-0 | 794 | 18 |
| e7 | 10 | 10 | 0.3 | Wax E 0.4 | V-0 | 978 | 14 |
| e8 | 10 | 10 | 0.3 | Wax OP 0.4 | V-0 | 966 | 14 |

What is claimed is:

1. A mixture comprising: 1) 5 to 90% by weight of a phosphonite (component A), 2)5 to 90% by weight of a mixture comprising an ester of mono(montan wax acid) and 1,3-butanediol, an ester of di(montan wax acid) and 1,3-butanediol, montan wax acids, 1,3-butanediol, and calcium montanate, and 3)5 to 90% by weight of a carboxylic-amide (component C).

2. The mixture as claimed in claim 1, wherein the phosphonite is a phosphonite of the structure $$R-[P(OR_1)_2]_m \quad (I)$$

where

R is a mono- or polyvalent allphatlc, aromatic, or heteroaromatic organic radical, and $R_1$ Is a group of the structure (II)

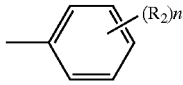

(II)

or the two radicals $R_1$ form a bridging group of the structure (III)

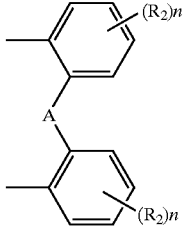

(III)

where

A is a direct bond, O, S, $C_{1-18}$-alkylene (linear or branched), or $C_{1-18}$-alkylidene (linear or branched), and where $R_2$ are, independently of one another, $C_{1-12}$-alkyl (linear or branched), $C_{1-12}$-alkoxy, or $C_{5-12}$-cycloalkyl, and n is 0 to 5, and m is from 1 to 4.

3. The mixture as claimed in claim 2, wherein

R is $C_{4-18}$-alkyl (linear or branched), $C_{4-18}$-alkylene (linear or branched), $C_{5-12}$-cycloalkyl, $C_{5-12}$-cycloalkylene, $C_{6-24}$-aryl or -heteroaryl, $C_{6-24}$-arylene or $C_{6-24}$-heteroarylene, which may also have further substitution;

$R_1$ is a group of the structure (II) or (III), where $R_2$ are independently of one another, $C_{1-8}$-alkyl (linear or branched), $C_{1-8}$-alkoxy, or cyclohexyl;

A is a direct bond, O, $C_{1-8}$-alkylene (linear or branched), $C_{1-8}$-alkylidene (linear or branched) and n is from 0 to 3 m is from 1 to 3.

4. The mixture as claimed in claim 2, wherein

R is cyclohexyl, phenyl, phenylene, biphenyl, or biphenylene $R_1$ is a group of the structure (II) or (III), where R$_2$ are independently of one another, C$_{1-8}$-alkyl (linear or branched), C$_{1-8}$-alkoxy, or cyclohexyl;

A is a direct bond, O, C$_{1-6}$-alkylidene (linear or branched) and n is from 1 to 3 m is from 1 to 2.

5. The mixture as claimed in claim 1, wherein component C is a derivative of an aromatic di- or tricarboxylic (ester) amide.

6. The mixture as claimed in claim 5, wherein the derivative is N,N'-bispiperidinyl-1,3-benzenedicarboxamide and/or N,N'-bis(2,2,6,6-tetramethyl-4-piperidinyl)-1,3-benzenedicarboxamide.

7. The mixture as claimed in claim 1, further comprising at least one phosphite of the formula (IV)

  (IV)

where R$_1$ is a group of the structure (II) or (III)

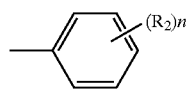  (II)

or the two radicals R$_1$ form a bridging group of the structure (III)

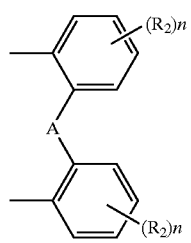  (III)

where

A is a direct bond, O, S, C$_{1-18}$-alkylene (linear or branched), or C$_{1-18}$-alkylidene (linear or branched), and where R$_2$ are, independently of one another, C$_{1-12}$-alkyl (linear or branched), C$_{1-12}$-alkoxy, or C$_{5-12}$-cycloalkyl, and n is 0 to 5, and m is from 1 to 4.

8. The mixture as claimed in claim 7, wherein the at least one phosphite has the structure (VII) or (VIII)

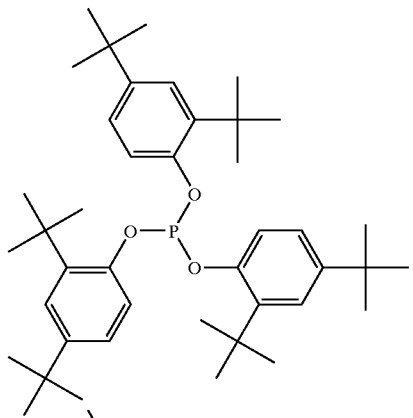

(VII)

(VIII)

9. The mixture as claimed in claim 1, wherein the phosphonite has the structure (V) or (VI)

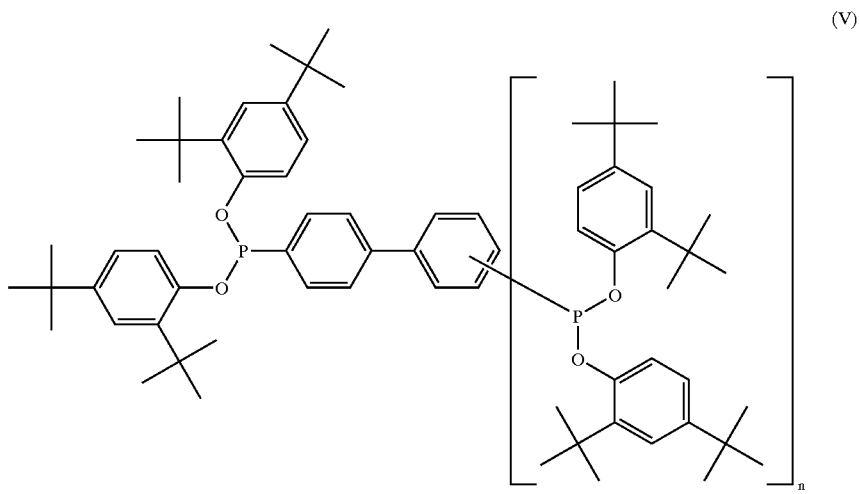

(V)

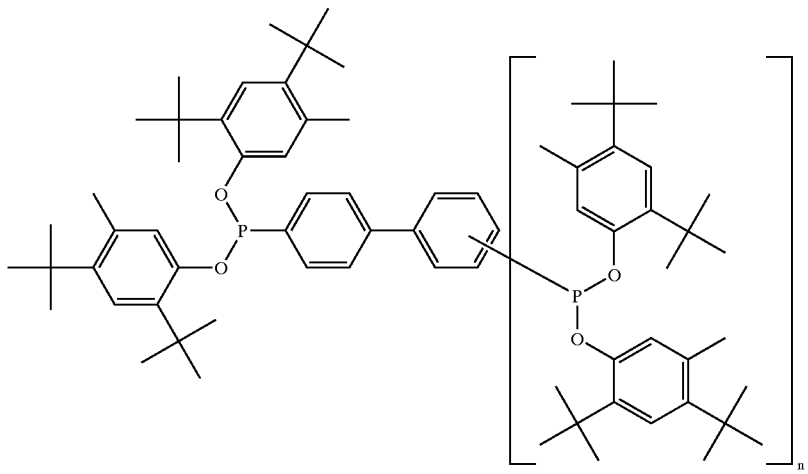

where n is 0 or 1.

10. The mixture as claimed in claim 1, which comprises from 15 to 70% by weight of component A, from 15 to 70% by weight of component B, and from 70 to 15% by weight of component C.

11. The mixture as claimed in claim 1, which comprises from 30 to 35% by weight of component A, from 30 to 35% by weight of component B, and from 35 to 30% by weight of component C.

12. The mixture as claimed claim 1, wherein components A, and B, C are present in a form selected from the group consisting of pellets, flakes, fine particles, powders, micronizates and mixtures thereof.

13. The mixture as claimed in claim 1, wherein components A, and B, C are present in a form selected from the group consisting of a physical mixture of the solids, a melt mixture, a compactate, an extrudate, and a masterbatch.

* * * * *